United States Patent [19]

Dürr et al.

[11] Patent Number: 5,125,840
[45] Date of Patent: Jun. 30, 1992

[54] ENOSSAL SINGLE TOOTH IMPLANT WITH TWISTING RESTRAINT

[75] Inventors: Walter Dürr, Remchingen; Axel Kirsch, Filderstadt, both of Fed. Rep. of Germany

[73] Assignees: Eberle Medizintechnische Element GmbH; IMZ-Fertigungs-und Vertriebs-Gesellschaft fuer dentale Technologie mbH, both of Fed. Rep. of Germany

[21] Appl. No.: 755,099

[22] Filed: Sep. 5, 1991

[30] Foreign Application Priority Data

Sep. 8, 1990 [DE] Fed. Rep. of Germany ....... 4028855

[51] Int. Cl.⁵ .............................................. A61C 8/00
[52] U.S. Cl. ................................................. 433/173
[58] Field of Search ....................... 433/173, 174, 175

[56] References Cited

U.S. PATENT DOCUMENTS

| | | | |
|---|---|---|---|
| 4,746,293 | 5/1988 | Lundgren et al. | 433/173 |
| 4,756,689 | 7/1988 | Lundgren et al. | 433/173 |
| 4,790,753 | 12/1988 | Fradera | 433/174 |
| 4,793,808 | 12/1988 | Kirsch | 433/173 |
| 4,850,870 | 7/1989 | Lazzara et al. | 433/173 |
| 4,872,839 | 10/1989 | Brajnovic | 433/173 |
| 4,955,811 | 9/1990 | Lazzara et al. | 433/173 |
| 5,026,280 | 6/1991 | Dürr et al. | 433/175 |
| 5,026,285 | 6/1991 | Dürr et al. | 433/173 |
| 5,040,982 | 8/1991 | Stefan-Dogar | 433/173 |
| 5,052,931 | 10/1991 | Kirsch | 433/173 |

Primary Examiner—John J. Wilson
Attorney, Agent, or Firm—Hill, Van Santen, Steadman & Simpson

[57] ABSTRACT

An enossal single tooth implant is constructed of a base member having a threaded axial bore for receiving a threaded base element, which has a head for clamping a spacer ring on the end of the base member characterized by the ring member and base body having coacting interlocking members, such as recesses and tongues to form an arrangement to prevent relative twisting of the ring member on the base body. The ring member can also be provided with interlocking elements that will coact with a tooth replacement to prevent twisting of the tooth replacement provided on the ring member, which replacement is held by a post which is received in a threaded bore of the base element.

9 Claims, 3 Drawing Sheets

ENOSSAL SINGLE TOOTH IMPLANT WITH TWISTING RESTRAINT

BACKGROUND OF THE INVENTION

The present invention is directed to an enossal single tooth implant, which is provided with a twisting restaint to enable a firm seating of a tooth replacement.

Enossal implants have been described in U.S. Pat. No. 4,793,808, whose disclosure is incorporated herein by reference thereto, and which claims priority from the same German Application as European Published Application 0 216 031. The implants disclosed in this Patent have proven satisfactory. However, a difficulty may occur when the implant is used as a single tooth implant because it is not possible to reliably prevent the tooth replacement from twisting or turning relative to a base body, unless the individual parts of the implant and the tooth replacement are bonded together. If these two parts are bonded together, difficulties may occur in the case of a subsequent replacement for either the tooth replacement or the implant post, if either fails due to breakage.

U.S. Pat. No. 5,026,285, whose disclosure is incorporated herein by reference thereto, and which claims priority from German Application P 39 17 690 discloses an enossal individual tooth implant and locking tool for use with the implant. This implant includes a base body which is implanted in the jaw bone and has a threaded bore for receiving a threaded member or base element of a spacer ring, which has an upper ring element or spacer bushing top for spacing an implant post from the base body. The base element has a bore for receiving the post for mounting the tooth replacement. In order to obtain a twisting restraint, the spacer bushing top or ring element of the pre-assembled base single tooth implant, according to U.S. Pat. No. 5,026,285, is constructed in a ring nut-like manner and can be threaded onto the base element by means of an interlocking thread with a much smaller pitch than the set thread of the spacer bushing bottom or base element, which are received in the base body. The base body and the spacer formed by the bushing top and the spacer bushing bottom can be locked and braced with one another, which leads to a twisting restraint of both the spacer bushing bottom receiving the implant post and the spacer bushing top. However, it does have the disadvantage, in certain uses, in that, in the case of locking with a special tool, the spacer bushing top and bottom must be secured against any relative rotation or twisting. Problems are sometimes encountered in operating such a special tool, particularly when the operator is relatively inexperienced.

SUMMARY OF THE INVENTION

The present invention is directed to providing an improvement of the implant device disclosed in U.S. Pat. No. 5,026,285, which improvement enables a simpler means for providing a reliable twisting restraint.

To accomplish these goals, the present invention is directed to an improvement in an enossal single tooth implant, which has a base body with a threaded bore for receiving a threaded base element of a spacer, which threaded base element holds a spacing ring member on the base body. The improvements are that the base body has an annular recess for receiving a proximal centering collar of the spacer ring member, which recess is provided with at least one interlocking member and the spacer ring member is provided with at least one corresponding interlocking member to cooperate with the interlocking member of the base body. An inner bore of the ring member has a counterbore to provide an inner stop shoulder. The base element at one end has a head portion, whose external diameter corresponds to the internal diameter of the counterbore of the ring member and forms an external stop shoulder complementary to the inner stop shoulder of the ring member so that the base element will hold the ring member on the base body.

Following the threading of the base element into the base body, the head of the base element will not project out of the counterbore of the ring member.

According to the invention, it is optional to also provide that the base body interlocking member or members have at least one axial base body interlocking pocket in a stop shoulder of the annular recess and that the spacer ring member has at least one interlocking tongue for being received in the recess.

According to another embodiment of the invention, the base body and the ring member are provided, in each case, with four interlocking members arranged in a uniform circumferential spacing.

It is also possible, according to the invention, for the inner threads of the spacer bushing base element to extend only over a distal portion of the total longitudinal dimensions thereof.

The invention also proposes that the spacer ring member, on its upper end has interlocking elements for a twisting restraint build-up of the tooth replacement mounted thereon. The build-up interlocking elements can have surface depressions and/or protuberances on the front edge and on the surface of the spacer bushing ring.

The invention also, optionally, proposes that the area of the circumferential surface of the ring member provided with the interlocking elements is constructed so as to taper conically in the distal direction. In addition, the spacer ring member can be constructed on its distal end as a polygonal fastening head for the tooth replacement build-up.

The invention is based on the surprising finding that it is possible without using special screwing and locking tools that are required for the single tooth implant according to U.S. Pat. No. 5,026,285 to obtain a reliable tooth twisting restraint, in that between the spacer bushing ring member and the base body is provided an interlocking connection securing solely in the rotational direction and which is, in turn, axially secured by means of the screw-like base element. The base element and the implant post which will be screwed into it are not twist-restraining relative to the base body, unless an additional bonding or cementing is carried out. However, the spacer ring member is reliably twist-restrained as a result of the interlocking connections with the base body so that a tooth replacement can be built up thereon in a twisting-restrained manner. The enossal single tooth implant according to the present invention is particularly suitable for twist-restrained structures.

The single tooth implant according to the invention is, naturally, also usable as a normal implant, for example for fixing bridges or the like, if particular significance is attached to the means for twisting restraint.

Other advantages and features of the invention will be readily apparent from the following description of the preferred embodiments, the drawings and claims.

DESCRIPTION OF THE PREFERRED EMBODIMENTS

Figure 2:
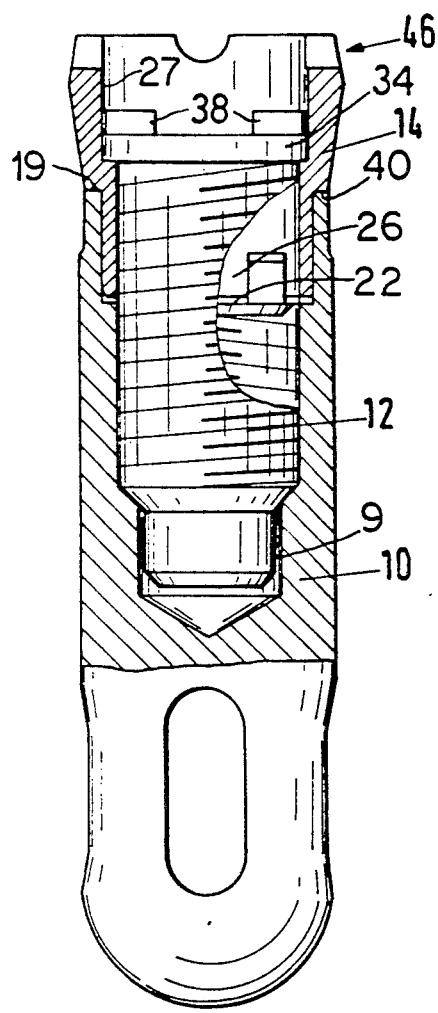
FIG. 2 is an elevational view with portions broken away and in cross section of the assembled elements forming the single tooth implant.

The principles of the present invention are particularly useful in an implant, generally indicated at 46 in FIG. 2, which is composed of a base body 10, a spacer assembly composed of a spacer bushing bottom or base element 12 and a spacer bushing top or ring member 14.

Figure 1:
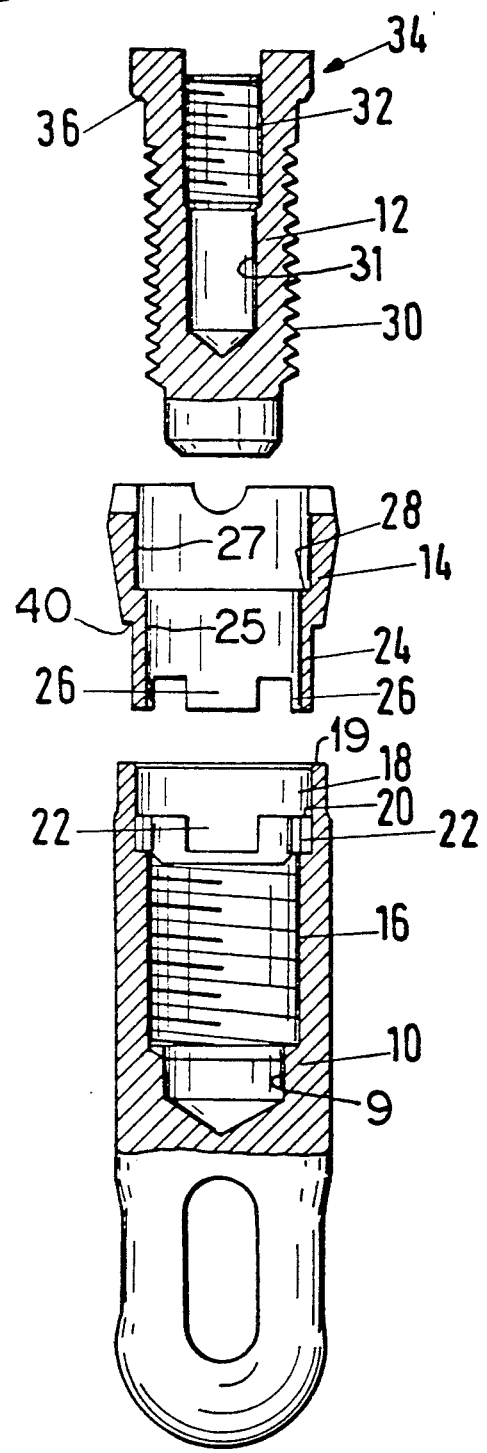
FIG. 1 is an exploded cross sectional view of an enossal single tooth implant according to the present invention, which is composed of a base body, a spacer ring and a base element.
Figure 5:
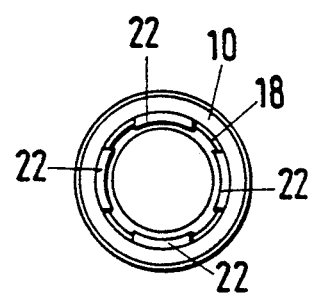
FIG. 5 is a top plan view of the base body of FIGS. 1 and 2.

As shown in FIGS. 1 and 2, the single tooth implant of the embodiment shown therein has a known base body 10, for example, such as disclosed in U.S. Pat. No. 5,026,280, which is made from a hydroxyapatite-coated titanium. The base body 10 is provided with an internal bore 9 that has internal threads 16. The base body 10 adjacent an upper edge or end 19, has a recess 18, which is of a larger diameter than the bore 9 to provide a stop shoulder 20. To provide means for preventing axial twisting, the stop shoulder 20 is provided with four uniformly, circumferentially spaced recess interlocking pockets 22 (illustrated in FIG. 5).

Figure 6:
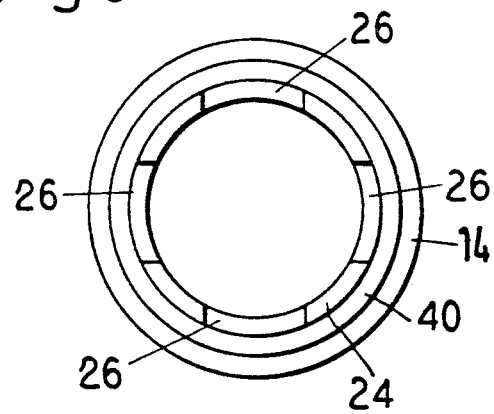
FIG. 6 is a bottom plan view of the ring element of FIGS. 1 and 2.

The spacer bushing top or ring member 14, at one end, is provided with a centering collar 24, whose external diameter corresponds to the annular recess 18 of the base body 10. The centering collar has four uniformly, circumferentially spaced interlocking tongues 26 (see FIG. 6), which are complementary to the interlocking pockets 22 of the base body and coact therewith to form the means for preventing twisting between the ring member 14 and the base body 10. The ring member 14 has an inner bore 25 with a large diameter counterbore 27, so as to provide an internal stop shoulder 28. The external surface of the spacer ring member 14 has an external stop shoulder 40 and, above this, is provided with an enlarged portion which tapers outwardly and then tapers inwardly.

The base element or spacer bushing bottom 12 is provided with external threads 30 which correspond to the internal threads 16 of the base body 10. The spacer bushing bottom or base element 12 is provided with an internal bore 31 having internal threads 32, which bore extends inward from a head portion 34 adjacent one end of the base element 12. The internal threads 32 can receive the implant post, as described in the above-mentioned U.S. Pat. No. 5,026,280. The large diameter head portion 34 forms an external shoulder 36, which is adjacent the upper end and which is complementary to the inner stop shoulder 28 of the ring member 14.

Figure 3:
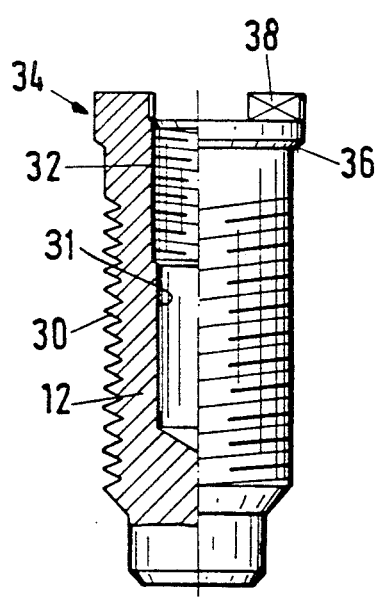
FIG. 3 is an elevational view with portions in cross section of the base element used in the assembly of FIG. 2.
Figure 4:
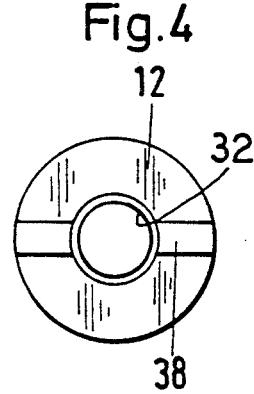
FIG. 4 is a top plan view of the base element of FIG. 3.

As best illustrated in FIGS. 3 and 4, the enlarged head 34 is provided with attachment webs or projections 38, which enable attachment of a tool which will thread the element 12 into the base body 10.

Figure 7:
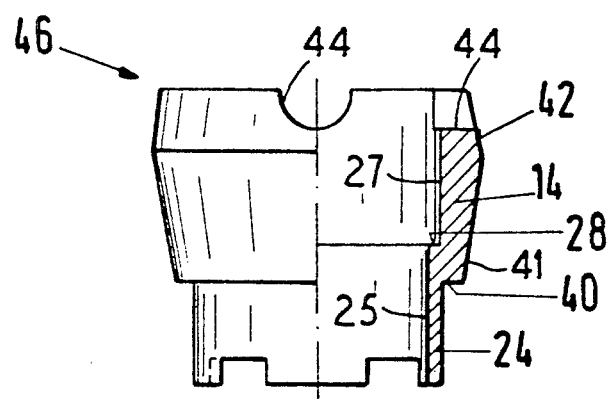
FIG. 7 is a elevational view with portions in cross section of the ring element utilized in the assembly of FIG. 2.
Figure 8:
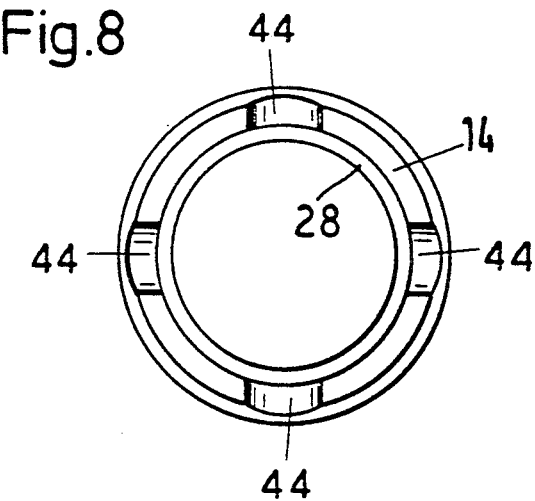
FIG. 8 is a top plan view of the ring element of FIG. 7.

The spacer bushing top or ring member 14, as best illustrated in FIG. 7, has an external shoulder 40 which connects the centering collar 24 to the enlarged portion, which has a conical diverging middle portion and the conical converging upper portion 42. The upper portion 42 is provided with a plurality of interlocking elements 44, which are circumferentially spaced therearound. As illustrated in FIGS. 7 and 8, four of these elements 44 are in the form of recesses, which form means for preventing twisting between a tooth structure which is fitted on the ring member 14. While the interlocking means are illustrated as being recesses, they could also be in the form of projections or protuberances.

The above-described single tooth implant is assembled as follows: After the base body 10 is already held in the body tissue or jaw bone, the spacer bushing or ring member 14 is inserted thereon and, in conjuction with the interlocking pockets 22 and the interlocking tongues 26 bring about a twisting-restrained plug connection. The spacer bushing bottom or base element 12 is then threaded into the base body 10 with the shoulder 40 of the ring 14 being pressed against the distal circumferential edge 19 of the base body 10. The shoulder 36 of the element 12 will engage the internal shoulder 28 of the ring member 14 to clamp or hold the ring member 14 on the base body 10 and, due to the coaction of the recesses 22 and the projections or tongues 26, axial twisting between the ring 14 and the base body 10 is prevented. The known implant post for the tooth replacement build-up is then threaded into the internal threads 32 of the spacer or base element 12. Since the base element 12 is only threaded into the base body 10, the implant post is not itself arranged in a twist-resistant manner relative to the base body 10. A twisting-resistant fixing of the tooth replacement structure is formed by the coaction with the recesses 44 of the spacer bushing or ring member 14. It should be noted that in the assembled position, such as illustrated in FIG. 2, the head 34 of the element 12 is received entirely within the counterbore 27 of the ring member 14.

Although various minor modifications may be suggested by those versed in the art, it should be understood that we wish to embody within the scope of the patent granted hereon all such modifications as reasonably and properly come within the scope of our contribution to the art.

We claim:

1. In an enossal single tooth implant including a base body threaded base element and a ring member, said base body having a threaded axial bore for receiving said threaded base element for holding the ring member on the base body, the improvements comprising means for preventing relative twisting of the ring member on the base body, said means including a base body having an axial recess adjacent one end, said recess including at least one interlocking member, the ring member having a centering collar having at least one interlocking member complementary to the interlocking member in said recess, said ring member having an inner bore with a counterbore to produce an inner stop shoulder, said base element, at one end, being provided with a head to form an external stop shoulder to engage the internal stop shoulder of the ring member to hold the ring member with the centering collar inserted in the recess of the base body with the coacting interlocking members engaged to prevent twisting therebetween.

2. In an enossal single tooth implant according to claim 1, wherein the axial length of the head portion of the base element and the axial length of the counterbore of the ring member are dimensioned so that the head portion of the base element is completely received within the counterbore of the ring member.

3. In an enossal single tooth implant according to claim 1, wherein the base body in the recess area has an internal stop shoulder and the interlocking member is an interlocking pocket in said stop shoulder and the interlocking member of the ring member is an interlocking tongue received in said interlocking pocket.

4. In an enossal single tooth implant according to claim 1, wherein the base body and the ring member are provided with four uniformly, circumferentially spaced interlocking members.

5. In an enossal single tooth implant according to claim 1, wherein the base element has an internal bore extending inward from said head portion provided with internal threads adjacent said head portion.

6. In an enossal single tooth implant according to claim 1, wherein the ring member is provided on an upper end opposite the centering collar with an interlocking element for forming means to prevent twisting between a tooth replacement and said ring member.

7. In an enossal single tooth implant according to claim 6, wherein the interlocking element of the ring member is a series of depressions and protuberances on said upper end of the ring member.

8. In an enossal single tooth implant according to claim 7, wherein the circumferential surface of the ring member provided with the interlocking elements tapers conically in the distal direction.

9. In an enossal single tooth implant according to claim 6, wherein the interlocking elements on the upper end of the ring member is formed by the ring member having a polygonal fastening head.

* * * * *